United States Patent
Laguna et al.

[11] Patent Number: 5,871,698
[45] Date of Patent: Feb. 16, 1999

[54] CHEMICAL SENSING FLOW PROBE

[75] Inventors: George R. Laguna; Frank J. Peter; Michael A. Butler, all of Albuquerque, N. Mex.

[73] Assignee: Sandia Corporation, Albuquerque, N. Mex.

[21] Appl. No.: 642,005

[22] Filed: May 2, 1996

[51] Int. Cl.[6] .......................... G01N 21/29; G01N 21/31
[52] U.S. Cl. .......................... 422/82.05; 422/55; 422/58; 422/68.1; 422/81; 422/82.09; 422/257; 436/52; 436/164
[58] Field of Search .................. 422/82.05, 257, 422/81, 63, 55, 58, 68.01, 82.09; 436/43, 49, 50, 52, 164, 805

[56] References Cited

U.S. PATENT DOCUMENTS

| | | | |
|---|---|---|---|
| 4,240,751 | 12/1980 | Linnecke et al. | 356/409 |
| 4,837,161 | 6/1989 | Stevens et al. | 436/52 |
| 4,920,056 | 4/1990 | Dasgupta | 436/50 |
| 5,250,263 | 10/1993 | Manz | 422/81 |
| 5,368,725 | 11/1994 | Bredeweg et al. | 210/137 |
| 5,389,524 | 2/1995 | Larsen et al. | 435/29 |
| 5,494,640 | 2/1996 | Simon et al. | 422/82.05 |

*Primary Examiner*—Ponnathapura Achutamurthy
*Attorney, Agent, or Firm*—V Gerald Grafe

[57] ABSTRACT

A new chemical probe determines the properties of an analyte using the light absorption of the products of a reagent/analyte reaction. The probe places a small reaction volume in contact with a large analyte volume. Analyte diffuses into the reaction volume. Reagent is selectively supplied to the reaction volume. The light absorption of the reaction in the reaction volume indicates properties of the original analyte. The probe is suitable for repeated use in remote or hostile environments. It does not require physical sampling of the analyte or result in significant regent contamination of the analyte reservoir.

13 Claims, 7 Drawing Sheets

5,871,698

CHEMICAL SENSING FLOW PROBE

This invention was made with Government support under Contract DE-AC04-94AL85000 awarded by the U.S. Department of Energy. The Government has certain rights in the invention.

BACKGROUND OF THE INVENTION

This invention relates to the field of chemical probes, specifically chemical probes using analyte/reagent reactions and light absorption characteristics to determine chemical concentrations.

The measurement of the concentration of a particular chemical in a fluid mixture is a task common to many industrial and commercial processes. Historically, measurement has required physical sampling of a portion of the fluid mixture (the analyte). A reagent is reacted with the analyte sample, and the resulting properties (e.g., color) of the reaction products indicates the concentration of the chemical of interest. Such procedures are well known to those skilled in the art. Many processes and environments, however, make physical sampling and remote chemical analysis problematic. Physical samples are very difficult to obtain from hazardous, radioactive, or borehole environments.

Instruments have been proposed for analysis near the analyte source. Examples include the instruments described in Bredeweg, U.S. Pat. No. 5,368,725, Manz, U.S. Pat. No. 5,250,263, Stevens, U.S. Pat. No. 4,837,161, and Larsen, U.S. Pat. No. 5,389,524. Unfortunately, these instruments suffer from numerous shortcomings that decrease their usefulness in many applications. They all require the direct flow of analyte through the instrument. Stevens measures the properties of an analyte stream after intentional contamination with a reagent, limiting its use to applications where reagent contamination of a relatively low analyte volume is acceptable. Larsen requires a discrete, physical volume sample of analyte, a difficult operation in many remote environments. Other instrument designs are incapable of remote reagent/analyte reaction or remote analysis of the reaction products. Many also have impaired accuracy because the analyte/reagent reaction does not occur in the same volume as the analysis of the reaction products.

Accordingly, there is a need for a compact instrument that can determine chemical concentrations without requiring physical sampling of the analyte, and that is suitable for remote operation.

SUMMARY OF THE INVENTION

The present invention provides a chemical probe that can determine the concentration of given chemicals in a fluid. The chemical probe has a reaction volume wherein the fluid to be analyzed (the analyte) can react with a known reagent. The chemical probe has means for launching light into the reaction volume, through the analyte/reagent reaction, to a collection point. The collected light can be analyzed to determine absorption properties of the analyte/reagent reaction, allowing determination of the concentration of the chemicals of interest in the analyte. The chemical probe allows the reaction volume to be flushed of the previous reaction, allowing multiple unattended measurements. The probe also provides for relatively slow analyte transport into the reaction volume and reagent transport out of the reaction volume, allowing measurements to be made directly in a large source of analyte without significantly contaminating the analyte. The chemical probe is well suited for in situ measurements because it can be made more compactly than previous chemical probes.

BRIEF DESCRIPTION OF THE DRAWINGS

The accompanying drawings, which are incorporated into and form part of the specification, illustrate embodiments of the invention and, together with the description, serve to explain the principles of the invention.

DETAILED DESCRIPTION OF THE INVENTION

The present invention provides an improved chemical sensing flow probe for the sensing of chemical concentrations based on light absorption by reagent/analyte in reaction.

Figure 1:
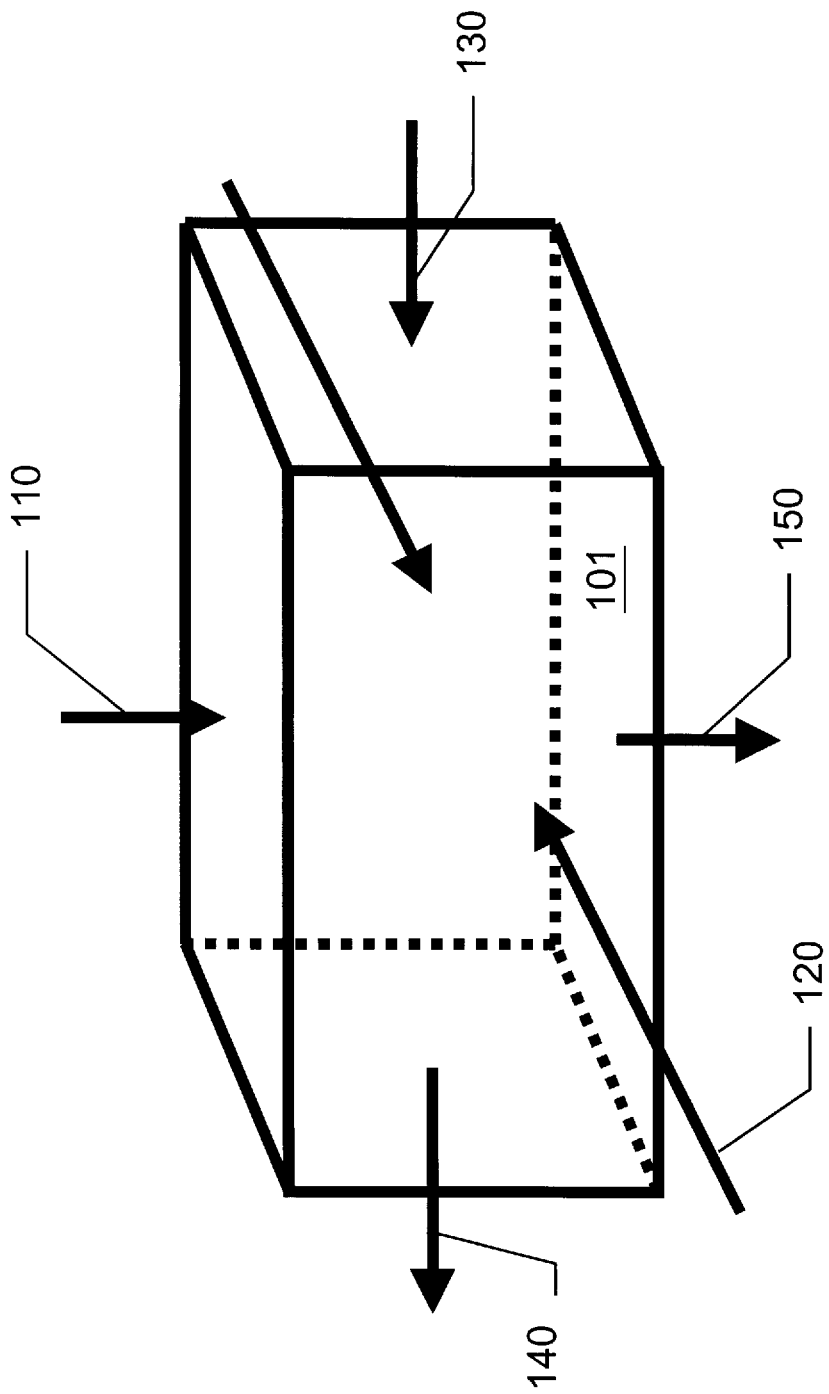
FIG. 1 is a simplified isometric view of a probe according to the present invention.

FIG. 1 is a simplified diagram of a probe according to the present invention. Reaction volume 101 connects with reagent input means 110 for introducing a reagent into the reaction volume, analyte means 120 for introducing a chemical to be analyzed (the analyte) into the volume, flush means 150 for flushing the residue of the reaction, light launch means 130 for launching light into the reaction volume, and light collection means 140 for collecting light from the reaction volume. In operation, a reagent is introduced into the reaction volume 101 via the reagent means 110. Analyte is introduced into the reaction volume 101 via the analyte means 120. As the reagent and analyte react, the light absorption properties of the fluid in the reaction volume 101 will change. The change in absorption properties can be determined by launching light into the reaction volume 101 via the light launch means 130 and collecting the light via the light collection means 140 after the light passes through the reaction volume 101. The determination can be done when the reaction is complete or in time as the analyte flows in to the reaction volume. The reagent can be chosen so that the reaction product's absorption properties vary based on the concentrations of predetermined chemicals in the analyte. The absorption of the launched light, as measured by the collected light, can thus be used to determine the relative concentrations of predetermined chemicals in the analyte. The reaction products can then be flushed from the reaction volume via flush means 150, and a new determination made by introducing new reagent and analyte into the reaction volume 101.

Figure 2:
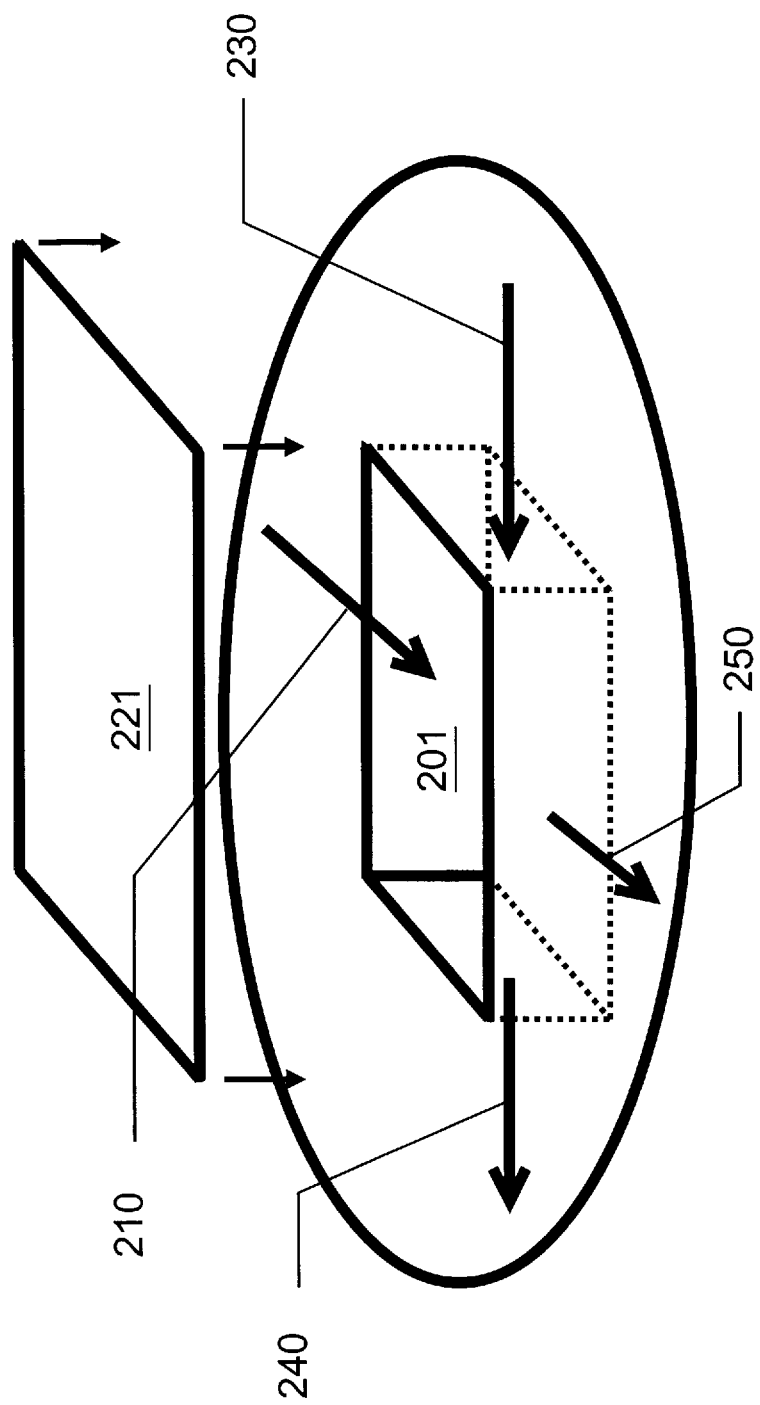
FIG. 2 is an exploded isometric view of a chemical probe according to the present invention.

FIG. 2 shows one embodiment of a chemical probe according to the present invention. A reaction volume 201 is formed in a bulk material 202. Reagent input means 210, flush means 250, light launch means 230, and light collection means 240 all connect with the reaction volume. A permeable membrane 221 covers one surface of the reaction volume 201.

The probe of FIG. 2 operates similarly to that discussed in FIG. 1. The probe can be placed in contact with an analyte sample volume (not shown) so that analyte in the sample volume (not shown) wets the permeable membrane 221. The permeable membrane 221 allows analyte to diffuse into the reaction volume 201 while preventing the rapid escape of reagent from the reaction volume 201. The average concentration of analyte in the reaction volume for times immediately following the reaction volume flush is given by:

$$A=(F_a*t)/V_{rv}$$

where:

A is the average concentration of the analyte in the reaction volume;

$F_a$ is the analyte flow rate through the permeable membrane;

t is the elapsed time; and $V_{rv}$ is the volume of the reaction volume.

Similarly, the average concentration of reagent in the analyte sample volume is given by:

$$R=(F_{rv}*t)/V_{ar}$$

where:

R is the average concentration of the reagent in the analyte sample volume;

$F_{rv}$ is the reagent flow rate through the permeable membrane;

t is the elapsed time; and $V_{ar}$ is the volume of the analyte sample volume.

If the flow rates $F_a$ and $F_{rv}$ are similar, then the average analyte concentration A in the reaction volume is greater than the average reagent concentration R in the analyte sample volume roughly proportional to the ratio of volume of the reaction volume to the volume of the analyte sample volume. If the probe is used to measure analyte properties in sample volumes much larger than the reaction volume, then suitable analyte-reagent reactions can be obtained with negligible reagent contamination of the analyte sample volume.

The intended use of the probe governs the choice of permeable membrane. In general, high analyte permeability and selectivity and low reagent permeability are desirable. The membrane must also be stable enough for the intended environment and use life. Reaction volumes roughly 5 mm along the optical path, ½ mm wide, and ½ mm deep are suitable for use in many applications. Analyte sample volumes typically contain many gallons of analyte.

Figure 3:
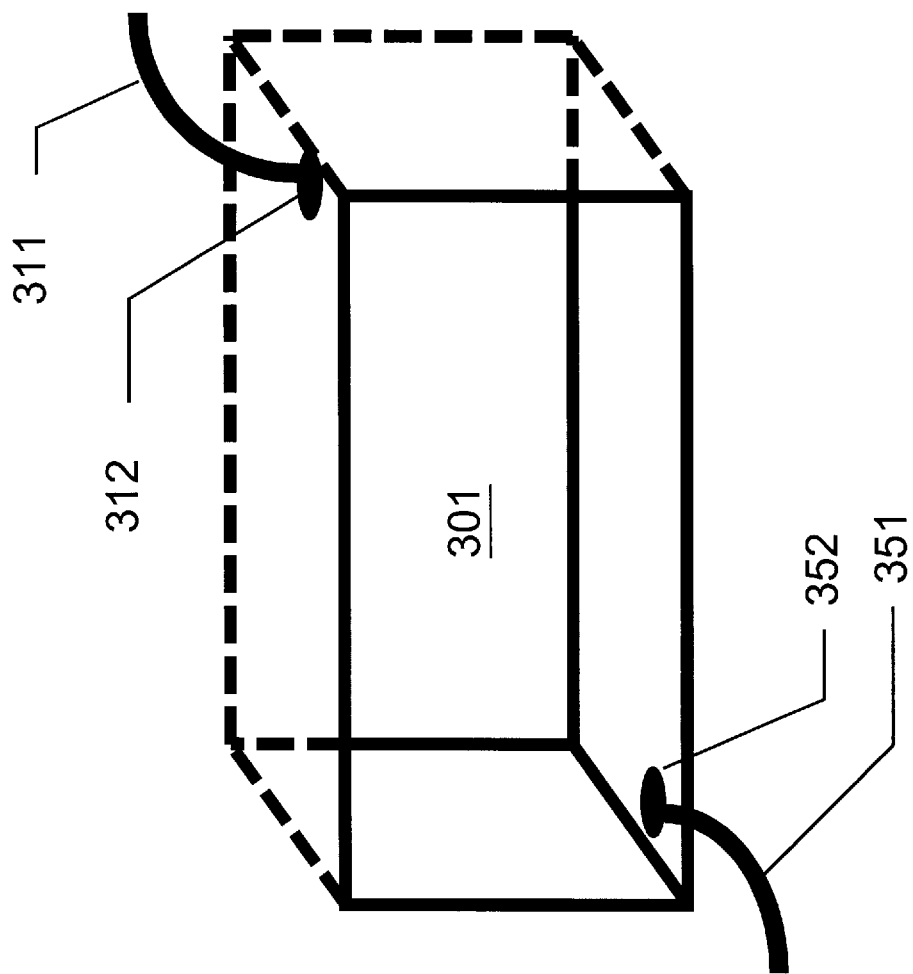
FIG. 3 is an isometric view of reagent means and flush means suitable for use in a chemical probe according to the present invention.

FIG. 3 shows reagent means and flush means suitable for use in a chemical probe according to the present invention. A reagent supply tube 311 connects a reagent reservoir (not shown) with a reagent port 312 into a reaction volume 301. The reagent port 312 and reagent tube 311 are sized so that reagent can be flowed into the reaction volume 301 much faster than reagent can escape from the reaction volume 301 into the surrounding analyte (not shown). A flush tube 351 connects a flush reservoir (not shown) with a flush port 352 into the reaction volume 301. The flush tube 351 and flush port 352 are sized so that the analyte/reagent reaction products can be removed from the reaction volume much faster than analyte can enter the reaction volume 301 from the surrounding analyte (not shown). The reagent tube 311, the reagent port 312, the flush tube 351, and the reagent port 352 are long relative to their cross section so that the analyte/reagent reaction products in the reaction volume 301 will diffuse into them slowly relative to the time required to complete a test. Cross sections of about 1/20 relative to length provide suitably slow diffusion.

Figure 4:
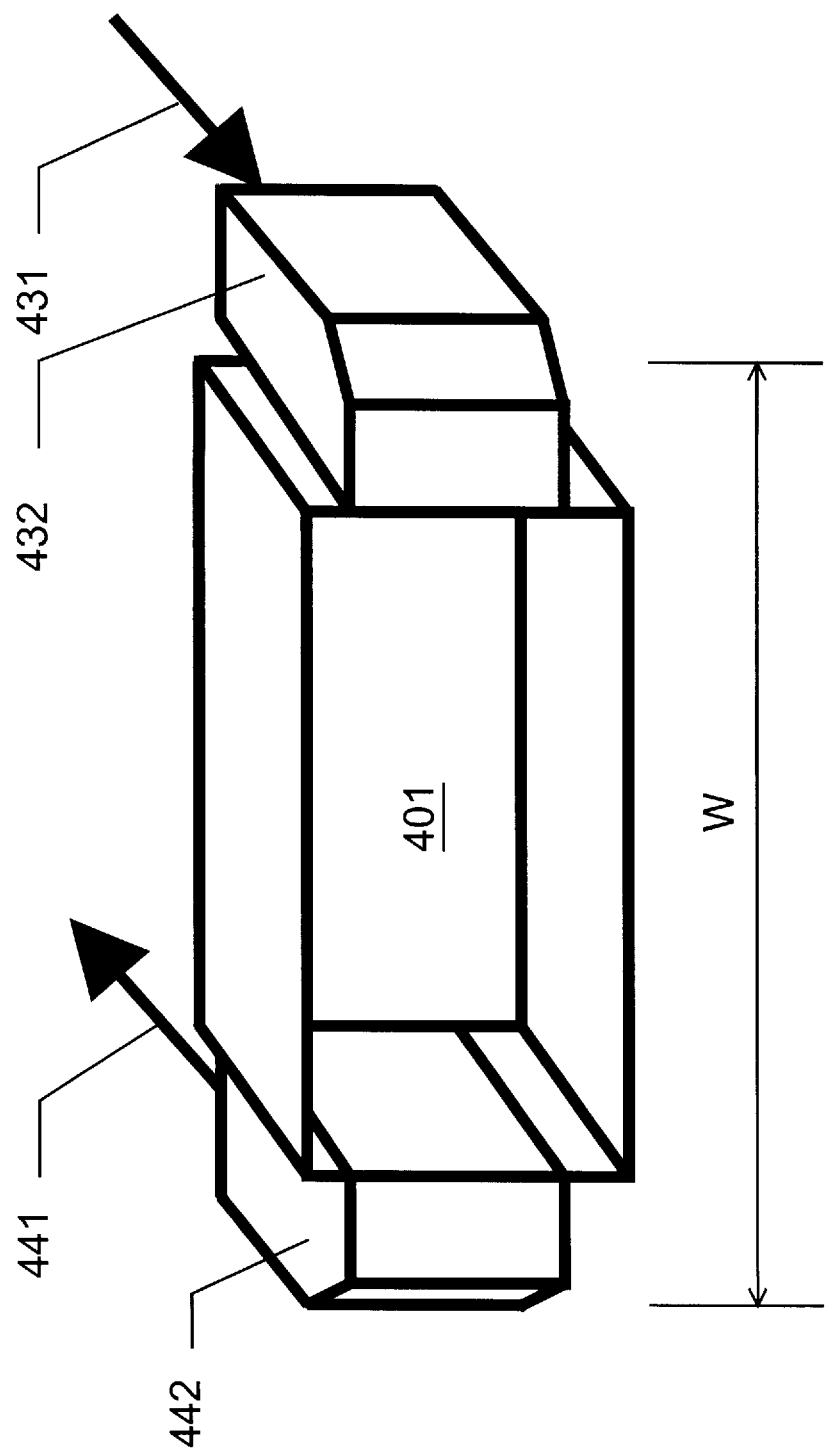
FIG. 4 is an isometric view of light launch means and light collection means suitable for use in a chemical probe according to the present invention.

FIG. 4 shows light launch means and light collection means suitable for use in a chemical probe according to the present invention. Light from an external light source (not shown) is routed to a launch prism 432 by routing means 431 such as optical fibers. The launch prism 432 reflects the light into the reaction volume 401. After traversing the reaction volume 401 and interacting with the analyte/reagent reaction products, the light enters a collection prism 442. The collection prism 442 reflects the light into routing means 441 such as optical fibers. The routing means 441 carry the light to an external analyzer (not shown) for analysis. The use of prisms 432, 442 to reflect the light allows the width W of the probe to be kept small, important for use in confined spaces, and also allows the depth D of the reaction volume to be kept small, such that analysis times can be less than 15 minutes.

Figure 5:
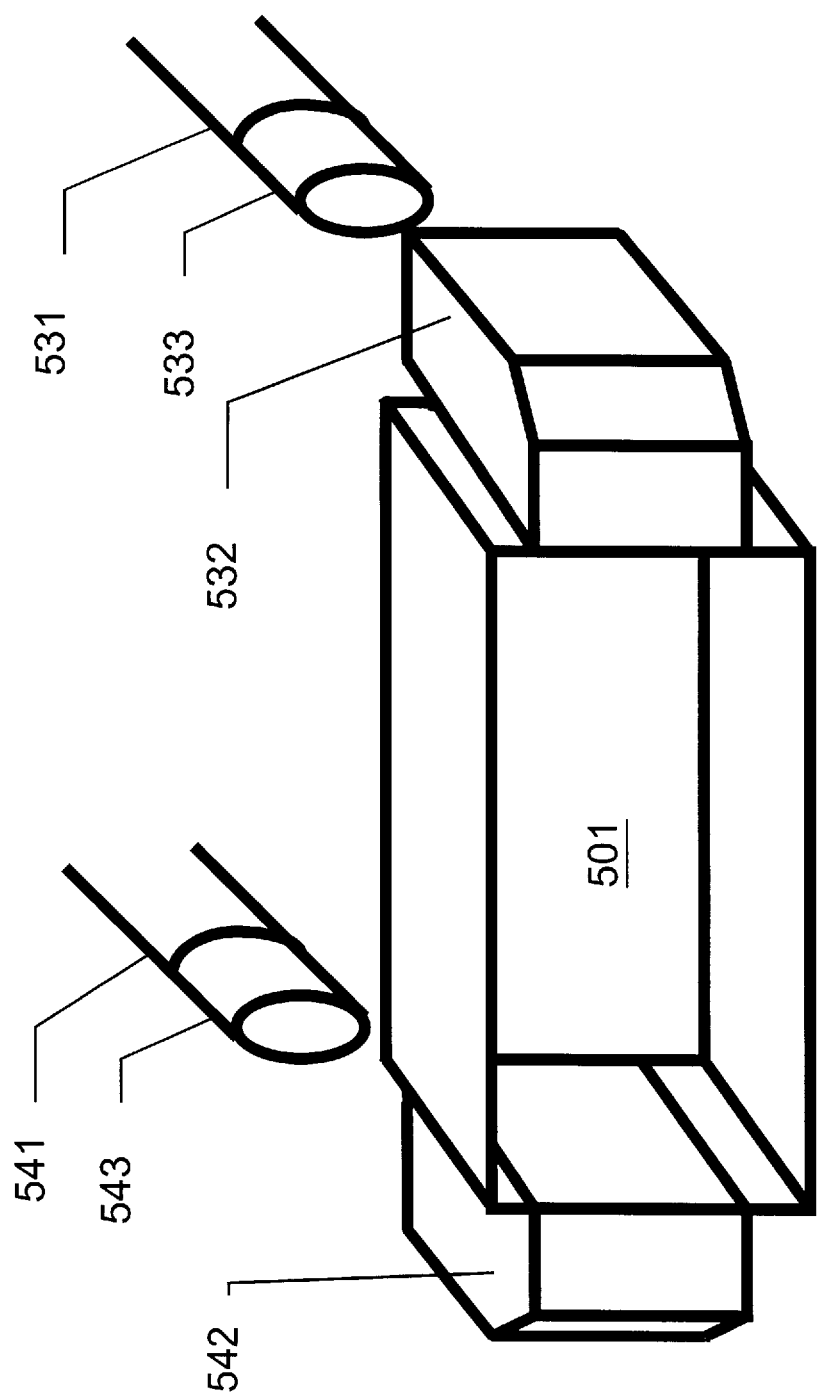
FIG. 5 is an isometric view of additional light launch means and light collection means suitable for use in a chemical probe according to the present invention.

FIG. 5 shows additional light launch means and light collection means suitable for use in a chemical probe according to the present invention. The probe in FIG. 5 is similar to that in FIG. 4, with the addition of lenses 533, 543. The lenses 533, 543 focus the light into prisms 532, 542, reducing the light energy lost in the coupling of light from optical fibers 531, 541 into prisms 532, 542. The selection of suitable lenses is known to those skilled in the art. Graded index lenses (Grin lenses) are suitable and have the additional benefit of small size.

Figure 6:
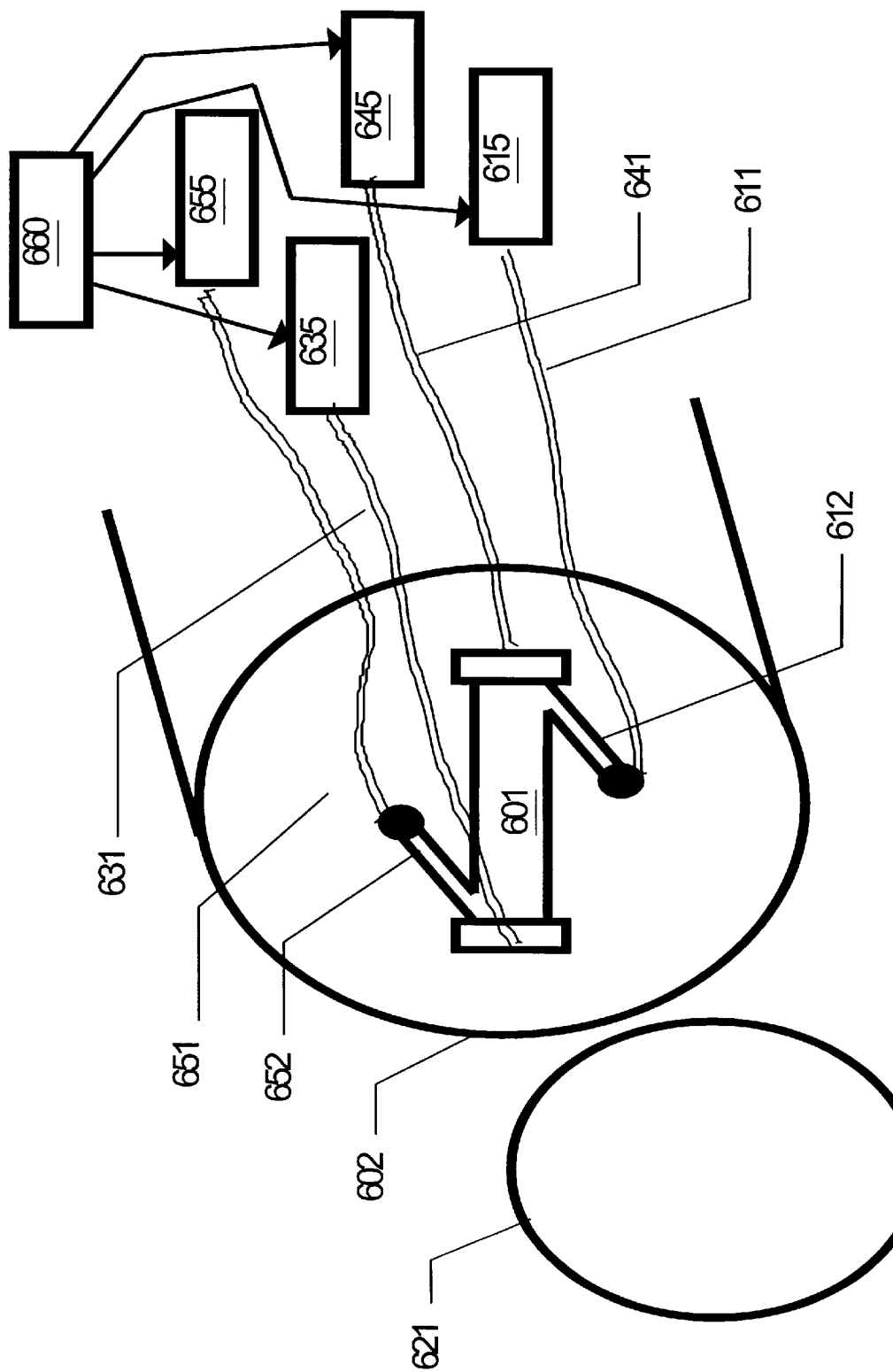
FIG. 6 is an isometric and schematic representation of a chemical probe according to the present invention.

FIG. 6 shows a chemical probe according to the present invention. A reaction volume 601 is at the end of a probe housing 602. A permeable membrane 621 mounts at one end of the probe housing 602, covering the reaction volume 601. A light source 635 connects with the reaction volume 601 via optical fiber 631. A light analyzer 645 connects with the reaction volume 601 via optical fiber 641. A reagent reservoir 615 connects with the reaction volume 601 via fill tube 611. A waste reservoir 655 connects with the reaction volume 601 via flush tube 651. The operation of the light analyzer 645, light source 635, fill reservoir 615, and waste reservoir 655 are coordinated by a control system 660. The spacing of fill tube 611, flush tube 651, and optical fibers 631, 641 around the periphery makes optimal use of the available space in the probe housing 602, allowing tight packing of the components into the probe. The resulting small size is important when the probe is to be used in confined spaces such as process pipes or wells. A fill channel 612 and a flush channel 652 direct the flow of reagent and reagent/analyte across the light entry and exit points. This flow generates a wiping action that helps keep the light path free from contamination (e.g., previous analyte/reagent reaction products).

The analyte and reagents of interest can affect the choice of reaction volume dimensions. As an example, one successful probe had a reaction volume about 0.1 in. long (along the direction of fluid flow), about 0.02 in. wide (normal to the direction of fluid flow), and about 0.02 in. deep (normal to the membrane surface). The fill and flush channels 612, 652 were about 0.02 in. wide (normal to the direction of fluid flow), about 0.02 in. deep (normal to the membrane surface), and about 0.1 in. long (along the direction of fluid flow).

Figure 7:
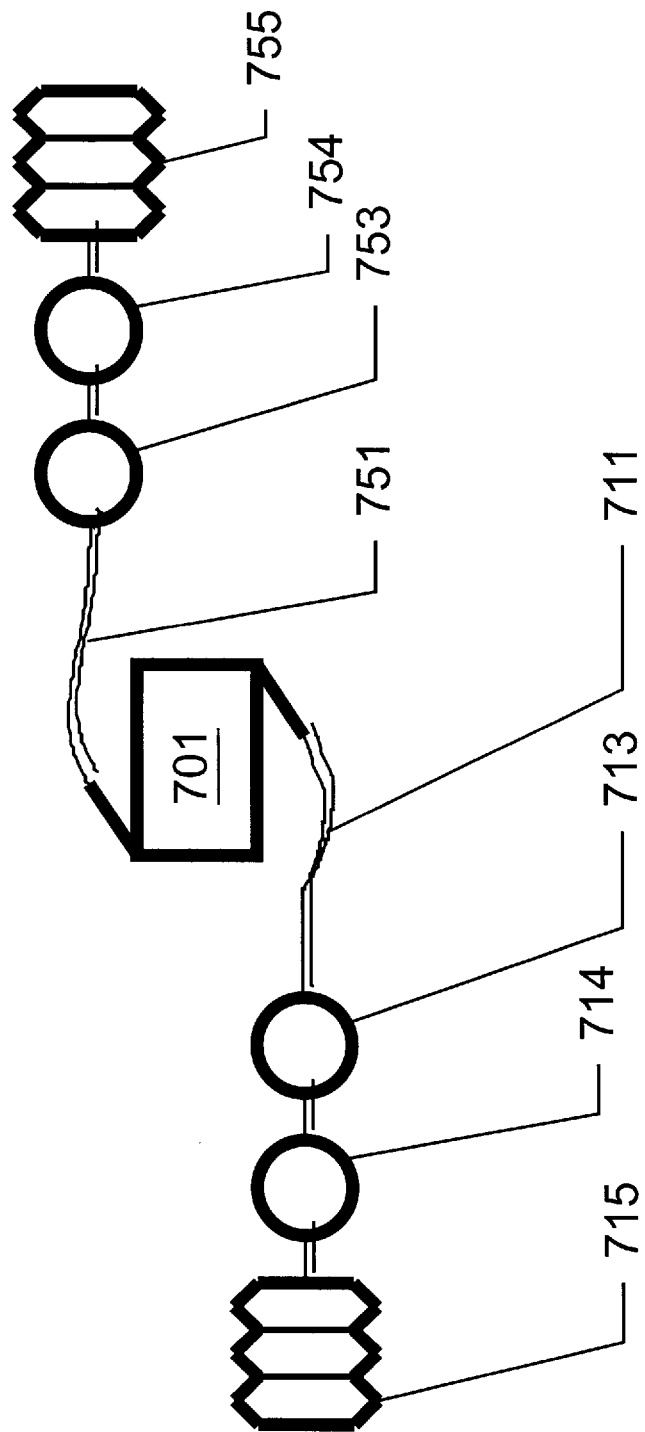
FIG. 7 is a schematic representation of the fluid portion of a chemical probe according of the present invention.

FIG. 7 is a schematic view of the reagent/waste portion of a chemical probe according to the present invention. A spring-loaded bellows reservoir 715 stores a quantity of reagent. The reservoir 715 can be filled via a fill port 714, such as a septum. Reagent flow through reagent fill tube 711 to the reaction volume 701 is controlled by a valve 713. The flow passes through a filter/frit 712, which controls the reagent flow rate and prevents particle contaminants from reaching the reaction volume 701. Reagent/analyte reaction products are carried from the reaction volume 701 to a spring-loaded bellows reservoir 755 through flush tube 751. Flow through flush tube 751 is controlled by a valve 753. Waste fluid can be removed from the reservoir 755 via a waste removal port 754 such as a septum. The use of spring-loaded bellows reservoirs places the fluid in the system under positive pressure. Positive pressure prevents the formation of bubbles, important because bubbles can dramatically change the light absorption characteristics of the fluid in the reaction volume and thus impair the accuracy of the probe. In operation, valve 753 opens first. After about one second, valve 713 opens, allowing fresh reagent into the reaction volume 701. After about 2 seconds, valves 713, 753 both close and the light absorption measurements are performed.

An implementation of the invention used 316 stainless steel for the probe housing to withstand corrosive reagents and analytes. An extremely thin stainless steel plate with 0.003 inch holes supported the membrane. The prisms were sapphire, with an optically polished surface finish and 10 wave flatness, with aluminum coated mirror surfaces. The reaction volume was about 0.02 inch wide and 0.02 inch deep. The fluid fittings were commonly available Swagelok SS-100-6 (and similar). Teflon tubing, 1/16 inch in diameter was used to connect the ports to the reservoirs. Suitable bellows reservoirs can be designed and fabricated by those skilled in the art to match the desired application. Manual valves from Hamilton Valve and solenoid valves from Valcor (SV20-1-1) were used to control the fluid flow. A Hammamatsu C3684 power supply powered a Hammamatsu L4633 Xenon flash lamp used as an external light source. About 20 flashes from the Xenon lamp were used for each sample. The 20 flashes were triggered with multi-cycle electronics whose design is well known to those skilled in the art. An American Holographic Rainbow spectrometer analyzed the collected light. The system was controlled and results analyzed by an IBM-compatible portable computer equipped with suitable digital and analog interfaces.

The particular sizes and equipment discussed above are cited merely to illustrate particular embodiments of the invention. It is contemplated that the use of the invention may involve components having different sizes and characteristics as long as the principles of the invention are followed. It is intended that the scope of the invention be defined by the claims appended hereto.

We claim:

1. A chemical probe comprising:
   a) a sensor head defining a reaction volume having a shape with a perimeter;
   b) launch means for launching light into the reaction volume at a launch site on the perimeter of the reaction volume;
   c) collection means for collecting light from the reaction volume at a collection site on the perimeter of the reaction volume such that light traveling from the launch site to the collection site defines a light path through the reaction volume;
   d) a permeable membrane in fluid communication with said reaction volume and in fluid communication with a source of an analyte fluid;
   e) reagent means for introducing a reagent fluid into the reaction volume, comprising at least one opening through the perimeter of the reaction volume, and reagent supply means for supplying reagent to the opening; and
   f) determination means for determining at least one property of the combination of reagent fluid and analyte fluid in the reaction volume from the launched light and the collected light;
   wherein the opening is situated so that reagent flow into the reaction volume impinges on and flows across at least one of the launch site or the collection site.

2. The chemical probe of claim 1 wherein said permeable membrane is substantially parallel to said light path.

3. The chemical probe of claim 1 further comprising flush means for removing analyte and reagent from the reaction volume.

4. The chemical probe of claim 1 wherein the distance through the reaction volume along the light path is greater than any distance through the reaction volume orthogonal to the light path.

5. The chemical probe of claim 1 further comprising light input means for connecting to an external light source, and wherein the launch means comprises transmission means for accepting light from the light input means and prism means for accepting light from the transmission means and directing light into the reaction volume.

6. The chemical probe of claim 1 wherein the collection means comprises prism means for accepting light from the reaction volume and transmission means for accepting light from the prism input, and further comprising light output means for accepting light from the transmission means and for connecting to an external light analyzer.

7. The chemical probe of claim 1, wherein the reagent supply means maintains positive pressure on the reagent at the opening.

8. A chemical probe comprising:
   a) a sensor head defining a reaction volume having a shape with a perimeter;
   b) a sensor head defining a reaction volume having a shape with a perimeter;
   c) launch means for launching light into the reaction volume at a launch site on the perimeter of the reaction volume;
   d) collection means for collecting light from the reaction volume at a collection site on the perimeter of the reaction volume such that light traveling from the launch site to the collection site defines a light path through the reaction volume;
   e) a permeable membrane in fluid communication with said reaction volume and in fluid communication with a source of an analyte fluid;
   f) reagent means for introducing a reagent fluid into the reaction volume;
   g) flush means for removing analyte and reagent from the reaction volume, comprising at least one opening through the perimeter of the reaction volume and exhaust means for transporting analyte and reagent from the opening; and
   h) determination means for determining at least one property of the combination of reagent fluid and analyte fluid in the reaction volume from the launched light and the collected light;
   wherein the opening is situated so that reagent and analyte are preferentially drawn from the area in front of at least one of the launch site or the collection site.

9. The chemical probe of claim 8, wherein the exhaust means maintains positive pressure on the reagent and analyte at the opening.

10. The chemical probe of claim 8 wherein said permeable membrane is substantially parallel to said light path.

11. The chemical probe of claim 8 wherein the distance through the reaction volume along the light path is greater than distance through the reaction volume orthogonal to the light path.

12. The chemical probe of claim 8 further comprising light input means for connecting to an external light source, and wherein the launch means comprises transmission means for accepting light from the light input and prism means for accepting light from the transmission means and directing light to the reaction volume.

13. The chemical probe of claim 8 wherein the collection means comprises prism means for accepting light from the reaction volume and transmission means for accepting light from the prism input, and further comprising light output means for accepting light from the transmission means and for connecting to an external light analyzer.

* * * * *